United States Patent
Bergersen

(10) Patent No.: US 6,626,664 B1
(45) Date of Patent: Sep. 30, 2003

(54) SELF OPENING ORTHODONTIC APPLIANCE WITH OPENING ASSISTANCE

(75) Inventor: Earl O. Bergersen, Winnetka, IL (US)

(73) Assignee: Ortho-Tain, Inc., Winnetka, IL (US)

( * ) Notice: Subject to any disclaimer, the term of this patent is extended or adjusted under 35 U.S.C. 154(b) by 0 days.

(21) Appl. No.: 09/546,685

(22) Filed: Apr. 11, 2000

(51) Int. Cl.[7] ................................................. A61C 7/00
(52) U.S. Cl. ......................................................... 433/6
(58) Field of Search ........................... 433/6, 7, 24, 215, 433/19; 128/861, 848; 264/16

(56) References Cited

U.S. PATENT DOCUMENTS

| | | | | |
|---|---|---|---|---|
| 2,590,118 A | * | 3/1952 | Oddo, Jr. | 128/136 |
| 2,857,909 A | * | 10/1958 | Johnson | 128/861 |
| 3,848,335 A | | 11/1974 | Bergersen | |
| 3,898,746 A | | 8/1975 | Bergersen | |
| 3,939,598 A | | 2/1976 | Bergersen | |
| 3,950,851 A | | 4/1976 | Bergersen | |
| 4,073,061 A | | 2/1978 | Bergersen | |
| 4,114,614 A | * | 9/1978 | Kesling | 128/136 |
| 4,139,944 A | | 2/1979 | Bergersen | |
| 4,784,605 A | | 11/1988 | Bergersen | 433/6 |
| 4,799,884 A | | 1/1989 | Bergersen | 433/6 |
| 4,830,612 A | | 5/1989 | Bergersen | 433/6 |
| 4,898,535 A | | 2/1990 | Bergersen | 433/6 |
| 4,919,612 A | | 4/1990 | Bergersen | 433/6 |
| 5,037,294 A | | 8/1991 | Bergersen | 433/6 |
| 5,037,295 A | | 8/1991 | Bergersen | 433/6 |
| D323,215 S | | 1/1992 | Bergersen | D24/180 |
| 5,203,695 A | | 4/1993 | Bergersen | 433/6 |
| 5,415,542 A | * | 5/1995 | Kesling | 433/6 |
| 5,645,420 A | | 7/1997 | Bergersen | 433/6 |
| 5,876,199 A | | 3/1999 | Bergersen | 433/6 |

* cited by examiner

*Primary Examiner*—John J. Wilson
*Assistant Examiner*—Melba Bumgarner
(74) *Attorney, Agent, or Firm*—Sonnenschein Nath & Rosenthal

(57) ABSTRACT

An orthodontic appliance is provided which includes an upper tooth receiving trough and a lower tooth receiving trough which are hinged together at a posterior portion of the appliance. The hinge is constructed so that the appliance is self opening to cause the troughs to maintain contact with the teeth when the patient's mouth is open. The appliance is formed of a soft and sticky plastic material so that it will adhere closely to the patient's teeth. Surface features are provided on opposing surfaces of the troughs to prevent the troughs from sticking to one another when the appliance is closed. An interference area is provided at the hinges to prevent the hinges from completely closing to assist in self opening of the appliance.

21 Claims, 1 Drawing Sheet

SELF OPENING ORTHODONTIC APPLIANCE WITH OPENING ASSISTANCE

BACKGROUND OF THE INVENTION

This invention relates to tooth straightening and retention appliances and a method for their use.

Removable orthodontic appliances are well known and a number of different constructions are disclosed in my prior patents such as U.S. Pat. Nos. 3,848,335; 3,898,736; 3,939,598; 3,950,851; 4,073,061; 4,139,944; 4,784,605; 4,799,884; 4,830,612; 4,898,535; 4,919,612; 5,037,294; 5,037,295; D323,215; 5,203,695; 5,645,420 and 5,876,199.

My previous removable appliances have been constructed with particular uses in mind including use by children having a deciduous dentition, mixed dentition and permanent dentition. Some of the appliances have provided for self opening of the appliance. Also, some appliances are intended to be worn at night. However, it would be an improvement if such appliances included features which would assist the appliance in adhering better to the wearer's teeth, as well as further assisting the opening of the appliance to permit breathing through the mouth, if necessary, to reduce the tendency for the appliance to be ejected from the mouth during sleep. It would also be an improvement if such an appliance were useful in correcting conditions such as overbite, overjet and crowding, and could be used prior to, during and after the application of fixed appliances such as braces.

SUMMARY OF THE INVENTION

The present invention provides an improved removable preformed appliance which is made of extra-soft material with a large amount of plasticiser in it, which makes it very soft and sticky. This material construction allows the appliance to be stretched over crooked teeth and to be able to stick to the dried off teeth to adhere better than previous appliances. The appliance has an upper trough and a lower trough connected at a rear end with an openable hinge and the opposed surface of the troughs include several raised bumps or other surface features so that the two opposed surfaces are not completely planar. The surface features prevent a suction from forming between the opposed trough walls when the patient opens his or her mouth while sleeping. If a suction did form, the easy opening of the appliance when the mouth opens would be prevented. Thus, the surface features assist in the self opening of the appliance which makes the appliance easier to wear, assists in breathing through the appliance allows for better retention to the crooked teeth, and prevents the appliance from slipping out of the mouth at night while the patient is sleeping.

The extra-soft material of the appliance allows the appliance to be able to stick to the teeth while the patient is sleeping which permits the appliance to exert pressure on the teeth all night so the teeth can be straightened out from their rotated and crowded positions.

The appliance is constructed so that it does not extend rearward to cover the most posterior teeth, namely, the first and second permanent molars which erupt at ages 6–7 years (first permanent molars), and at ages 12–13 years (second permanent molars). This shortening of the appliance at the posterior end allows the erupting teeth to over erupt and automatically open the bite, thereby correcting a deep overbite. Since this overbite is the most difficult problem to correct in orthodontics, and is extremely time consuming, it saves about one year of active (with fixed braces) treatment.

Several different sizes of the preformed appliance are provided, as described in my prior patents, and a proper sized appliance is selected for a particular patient.

The present appliance, in an embodiment, also arranges the lower arch to be moved forward or advanced from where it ideally is supposed to be which makes the mandible be positioned in a forward direction and encourages it to be advanced with growth. In other words, the mandible is forced to grow forward into a more ideal position, relative to the maxilla, which corrects an excessive overjet. The overjet is also a difficult problem to correct and this procedure makes it easier for the orthodontist in his or her treatment of the patient.

The appliance of the present invention can correct overbite, overjet and rotations and crowding in a very short period of time (three to six months depending on the severity of the problems) which is then to be followed by a fixed appliance, that is, permanent brackets placed on the teeth by an orthodontist. The present appliance can then continue to be worn by the patient, but by the placement of bands or brackets fixed to the most posterior teeth (the first or second adult molars) with arch wires, their vertical eruption is stopped and no further overbite is or will be corrected. The overjet, however, will still be corrected, if needed, by the relation of the upper and lower jaws of the patient. This correction has nothing to do with the eruption of the teeth. When the overjet is properly corrected, the correction simply stops, even though the wear of the appliance continues.

According to a method of the present invention, the appliance is worn after the braces go on to the patient and the soft material and thinness of the outer margins allow the appliance to fit over the brackets without trimming. Therefore, the outer margins, especially the labial and buccal margins are thinned to be more pliable, particularly since the plastic is so soft.

In an embodiment, an extra amount of interference is provided in the front of the hinge portion of the appliance to cause interference when the opened appliance is attempted to be closed. This allows the hinge portion to be quite resistant to closure even though the material is so soft. This keeps the appliance open when the patient opens his or her mouth while sleeping, and tends to keep the appliance in constant contact with the front teeth while the patient is asleep. This improves tooth and jaw movement and is critical to being able to straighten the teeth while sleeping.

The present invention will also accept additional plastic or rubber denture lining materials (vinyl or latex, etc. liners) to be put inside the appliance to increase the hold on the teeth once the straightening is complete, or these materials can be placed in areas that are already straight while others continue to be straightened.

The use of additional materials, such as denture powder or other similar materials that increase the stickiness of the appliance to the teeth at night can be used for further enhancing the stickiness of the appliance.

DETAILED DESCRIPTION OF THE PREFERRED EMBODIMENTS

Figure 1:
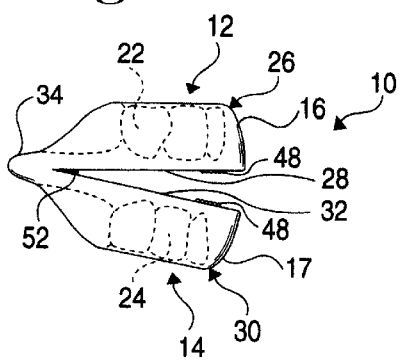
FIG. 1 is a side elevational view of an appliance embodying the principles of the present invention.
Figure 2:
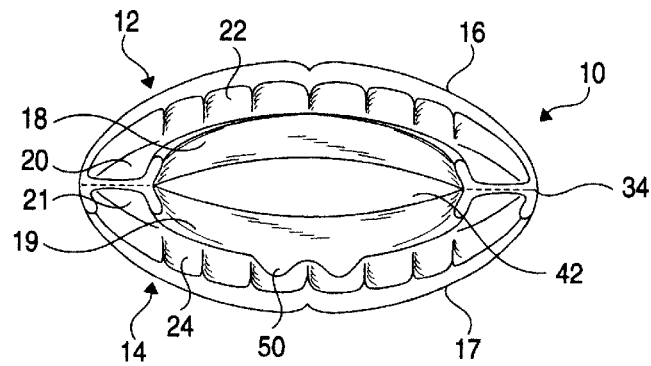
FIG. 2 is a lingual view of the appliance shown in FIG. 1.
Figure 3:
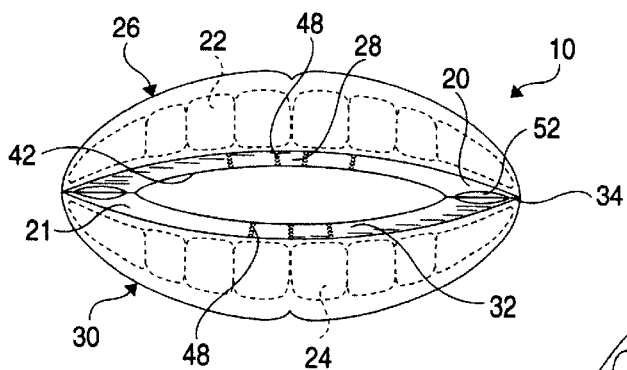
FIG. 3 is a front labial view of the device shown in FIG. 1.
Figure 4:
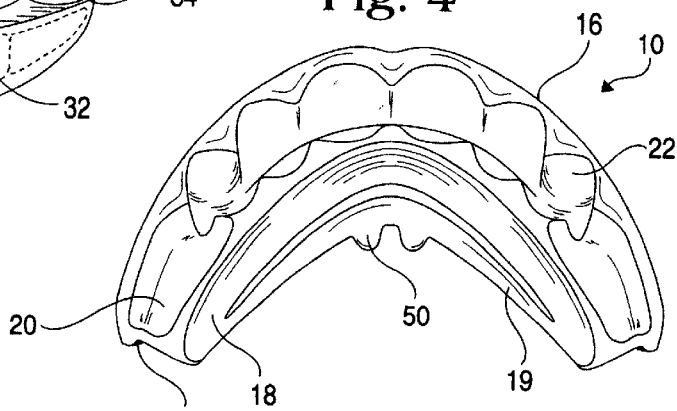
FIG. 4 is a plan view of the appliance shown in FIG. 1.
Figure 5:
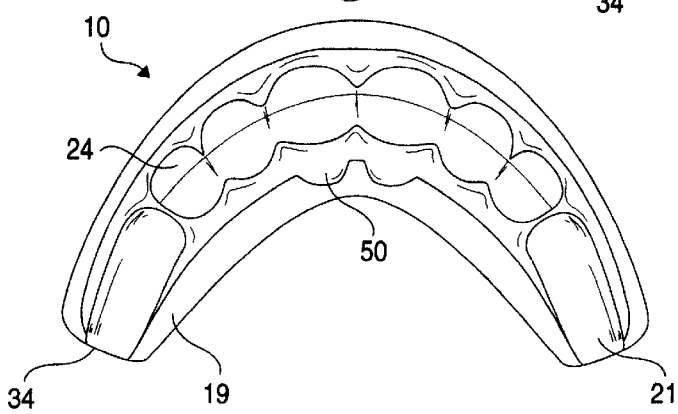
FIG. 5 is a bottom view of the appliance of FIG. 1.

FIGS. 1–5 illustrate an appliance constructed in accordance with the principles of the present invention and, generally, is an appliance having certain similarities in construction to various portions of appliances as disclosed in my prior patents cited above, each of which are incorporated herein by reference.

However, there are differences in the present construction providing improvements and enhancements which are described herein.

In general, an appliance is illustrated at 10 which includes an upper trough 12 for receiving the maxillary or upper row of teeth, and a lower trough 14 for receiving the mandibular or lower row of teeth. The troughs are formed generally by a labial-buccal flange 16, 17 and a lingual flange 18, 19. The flanges are connected by an isthmus portion 20,21. Both the upper and lower troughs are provided with tooth receiving depressions or sockets 22, 24. The appliance is partially split along a central parting line such that the upper trough 12 is in an upper portion 26 having a solid lower surface 28 formed by the slit and the lower trough 14 is in a lower portion 30 having an upper surface 32 formed by the slit. A connecting hinge portion 34 is formed at a posterior end of the appliance since the slit extends only partially through the appliance, thus leaving an anterior end of the upper part 26 and an anterior end of the lower part 30 separate from each other.

An aperture 42 is provided in a central part of the appliance which, when opened, acts as an air flow passage to permit the user to breath through this opening when the appliance is in the user's mouth.

Surface features 48 are provided on the lower surface 28 and upper surface 32 such that these two surfaces are not completely planar. The surface features may include bumps, ribs, undulations or other similar types of features such that the lower surface 20 and upper surface 32 are not complementary to each other, so there will always be spaces between the two surfaces, even when they are pressed together when the user has his or her mouth closed.

Lingual extensions 50 are provided on the lower trough 14 to assist in keeping the mandible of the individual advancing maximally at all times and moving forward. For producing a forward mandible force, the most important tooth margins are the lower lingual contact surface and the upper labial contact surface at the anterior portion of the appliance 10. It is therefore important that inferior or lower inner lingual surface 19 and superior upper labial surface 16 are supported by sufficient appliance material to maintain their relative positions when the appliance is inserted into an individual's mouth.

The appliance 10 is made of an extra-soft material with a large amount of plasticiser in it to make it very soft and sticky. Preferably the appliance has a durometer reading hardness as measured in the Shore A range in accordance with ASTM-D2240 in the range of 30–60, more preferably in the range of 35–50 and in a most preferred mode, 45. The hinge area 34 does not extend rearwardly enough to cover the most posterior teeth, namely, the first and second permanent molars for any particular patient. Also, the tooth receiving sockets 24 in the lower trough 14 are positioned forwardly in a horizontal orientation relative to the tooth sockets 22 in the upper trough 12 to cause the mandible to be positioned in a forward direction relative to the maxilla to correct excessive overjet. Although the appliance is most useful with children, beginning about age 7, after the eruption of the first permanent molars, the appliance can be used with success with adults as well. In a preferred method of use of the appliance, it is worn only at night, and can be worn prior to, during and following the use of fixed brackets or braces.

The labial and buccal flanges 16, 17 are formed of soft material and are relatively thin so as to be pliable so that the appliance can be worn even over fixed braces or brackets applied by an orthodontist. The flanges may have a thickness in the range of 0.5 to 2 mm, and preferably are thicker at their free ends (which will be adjacent the patient's gum line) and thinner near the isthmus portions 20, 21 (which will be near the crowns of the patient's teeth).

An extra amount of material is applied at the hinge area as shown at location 52 in FIG. 1 to cause interference between the lower surface 28 and the upper surface 32 when the opened appliance 10 is attempted to be closed. This allows the hinge portion 34 to be quite resistant to closure even though the material of the appliance is soft. This extra interference material at 52 helps keep the appliance open when the patient opens his or her mouth while sleeping and tends to keep the appliance in constant contact with the front teeth while the patient is asleep.

The upper and lower tooth receiving troughs will accommodate additional plastic or rubber denture lining materials to be placed therein to increase the hold on the teeth once the straightening is complete.

Use of the appliance can be started about 3 to 6 months prior to the placement of the fixed appliances. This will allow the overbite to be corrected and partially correct most on all of the overjet by mandibular advancement. If the overbite or overjet is severe, more than 6 months of night time wear may be required. About 1 mm per month of correction takes place. Full overbite correction should be obtained before molar bands or brackets and arch wires are placed. Once the limited fixed appliances are placed (usually for incisal torque, rotations and crowding) the appliance can be adjusted (by trimming the interior are of the sockets) to allow the brackets and the arch wires to fit better. The appliance can be worn while the brackets are on the teeth to aid in the retention of the overbite and to continue the mandibular advancement if necessary. The appliance stops the mandibular advancement once the ideal jaw relation is obtained. The same appliance can be used as a retainer once the brackets are removed.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An orthodontic appliance for use in the positioning of teeth comprising:

a first tooth receiving trough in an upper portion for positioning an upper row of teeth, and a second tooth receiving trough in a lower portion for positioning a lower row of teeth, said troughs being defined by lingual and labial-buccal flanges and including an isthmus interconnecting said flanges, said upper portion isthmus and said lower portion isthmus being separated at an anterior end of said appliance, but connected at a posterior end of said appliance to form a hinge connection between said two portions, said upper portion isthmus having a lower surface facing an upper surface of said lower portion isthmus, and at least one of said lower and upper surfaces having a surface feature thereon such that said surfaces are not complementary in shape;

said appliance being formed of an extra soft plastic material having a durometer reading hardness, as measured in the Shore A range in accordance with ASTM-D2240, in the range of 30–50.

2. An orthodontic appliance according to claim 1, wherein said surface feature comprises bumps formed on at least one of said upper and lower surfaces.

3. An orthodontic appliance according to claim 1, wherein said surface feature comprises ridges formed on both said upper and lower surfaces.

4. An orthodontic appliance according to claim 1, wherein said tooth receiving troughs terminate in a rearward direction at a point short of the first permanent molar of a wearer.

5. An orthodontic appliance according to claim 1, wherein said lower lingual flange includes an extension.

6. An orthodontic appliance according to claim 1, wherein said appliance is very flexible and sticky relative to dried teeth surfaces.

7. An orthodontic appliance for use in the positioning of teeth comprising:
- a first tooth receiving trough in an upper portion for positioning an upper row of teeth, and
- a second tooth receiving trough in a lower portion for positioning a lower row of teeth,
  - said troughs being defined by lingual and labial-buccal flanges and including an isthmus interconnecting said flanges,
  - said upper portion isthmus and said lower portion isthmus being separated at an anterior end of said appliance, but connected at a posterior end of said appliance to form a hinge connection between said two portions,
  - said upper portion isthmus having a lower surface facing an upper surface of said lower portion isthmus,
  - said hinge connection including an interference element preventing said upper portion isthmus and lower portion isthmus from pivoting completely toward one another along an entirety of said upper and lower surfaces;
  - said appliance being formed of an extra soft plastic material having a durometer reading hardness, as measured in the Shore A range in accordance with ASTM-D2240, in the range of 30–60.

8. An orthodontic appliance according to claim 7, wherein said interference element comprises an extra amount of material of said appliance provided on at least one of said upper portion isthmus lower surface and said lower portion isthmus upper surface adjacent and anterior of said hinge connection.

9. An orthodontic appliance according to claim 7, wherein at least one of said lower and upper surfaces has a surface feature thereon such that said surfaces are not complementary in shape.

10. An orthodontic appliance according to claim 9, wherein said surface feature comprises bumps formed on at least one of said upper and lower surfaces.

11. An orthodontic appliance according to claim 9, wherein said surface feature comprises ridges formed on both said upper and lower surfaces.

12. An orthodontic appliance according to claim 7, wherein said appliance is very flexible and sticky relative to dried teeth surfaces.

13. An orthodontic appliance according to claim 7, wherein said tooth receiving troughs terminate in a rearward direction at a point short of the first permanent molar of a wearer.

14. An orthodontic appliance according to claim 7, wherein said lower lingual flange includes an extension.

15. An orthodontic appliance for use in the positioning of teeth comprising:
- a first tooth receiving trough in an upper portion for positioning an upper row of teeth, and
- a second tooth receiving trough in a lower portion for positioning a lower row of teeth,
  - said troughs being defined by lingual and labial-buccal flanges and including an isthmus interconnecting said flanges,
  - said upper portion isthmus and said lower portion isthmus being separated at an anterior end of said appliance, but connected at a posterior end of said appliance to form a hinge connection between said two portions,
  - said upper portion isthmus having a lower surface facing an upper surface of said lower portion isthmus,
  - said appliance being formed of an extra soft plastic material having a durometer reading hardness, as measured in the Shore A range in accordance with ASTM-D2240, in the range of 30–60, which material is very flexible and sticky relative to dried teeth surfaces;
  - said hinge connection including an interference element comprising an extra amount of material of said appliance provided on at least one of said upper portion isthmus lower surface and said lower portion isthmus upper surface adjacent and anterior of said hinge connect, which interference element prevents said upper portion isthmus and lower portion isthmus from pivoting completely toward one another along an entirety of said upper and lower surfaces.

16. An orthodontic appliance according to claim 15, wherein at least one of said lower and upper surfaces has a surface feature thereon such that said surfaces are not complementary in shape.

17. An orthodontic appliance according to claim 16, wherein said surface feature comprises bumps formed on at least one of said upper and lower surfaces.

18. An orthodontic appliance according to claim 16, wherein said surface feature comprises ridges formed on both said upper and lower surfaces.

19. An orthodontic appliance according to claim 15, wherein said tooth receiving troughs terminate in a rearward direction at a point short of the first permanent molar of a wearer.

20. An orthodontic appliance according to claim 15, wherein said lower lingual flange includes an extension.

21. An orthodontic appliance for use in the positioning of teeth comprising:
- a first tooth receiving trough in an upper portion for positioning an upper row of teeth, and
- a second tooth receiving trough in a lower portion for positioning a lower row of teeth,
  - said troughs being defined by lingual and labial-buccal flanges and including an isthmus interconnecting said flanges,
  - said upper portion isthmus and said lower portion isthmus being separated at an anterior end of said appliance, but connected at a posterior end of said appliance to form a hinge connection between said two portions,
  - said upper portion isthmus having a lower surface facing an upper surface of said lower portion isthmus, and at least one of said lower and upper surfaces having a surface feature thereon such that said surfaces are not complementary in shape;
  - said hinge connection including an interference element preventing said upper portion isthmus and lower portion isthmus from pivoting completely toward one another along an entirety of said upper and lower surfaces.

* * * * *